United States Patent [19]

Ollenberger

[11] 4,442,832

[45] Apr. 17, 1984

[54] THERAPEUTIC COUCH

[76] Inventor: Eugene Ollenberger, 4305 Francis St., Burnaby, British Columbia, Canada, V5C 2R2

[21] Appl. No.: 210,894

[22] Filed: Nov. 28, 1980

[51] Int. Cl.[3] .......... A61F 5/00

[52] U.S. Cl. .......... 128/71

[58] Field of Search .......... 272/121, 125, 145, 120; 5/61, 77, 62, 74, 76; 108/1, 5, 6; 128/70, 74, 75, 73, 71, 72, 84 R, 68, 24; 296/323

[56] References Cited

U.S. PATENT DOCUMENTS

| | | | |
|---|---|---|---|
| 2,887,691 | 5/1959 | Talarico et al. | 5/62 |
| 3,611,453 | 10/1971 | Lokken | 5/62 |
| 3,640,520 | 2/1972 | Weiland et al. | 5/62 |
| 3,797,050 | 3/1974 | Benoit | 5/62 |
| 3,997,926 | 12/1976 | England | 5/62 |
| 4,274,167 | 6/1981 | Immel | 5/62 |

*Primary Examiner*—Richard C. Pinkham
*Assistant Examiner*—T. Brown
*Attorney, Agent, or Firm*—Townsend and Townsend

[57] ABSTRACT

A therapeutic couch has a rectangular frame of which a padded bench is mounted to accommodate a person in the prone position. Legs at opposite ends of the frame support the padded bench a suitable distance above the floor. Straps are provided at the foot end of the padded bench to secure the ankles of the prone occupant against movement longitudinally of the frame. A lever assembly is fitted to the underside of the frame to fold and unfold hinge-fashion in rolling contact with the floor. The frame also supports a mechanism which is operable by the person on the bench to fold the assembly so that the bench is tilted at an acute angle to the floor and the occupant is held by the ankles in a head-down position.

7 Claims, 12 Drawing Figures

Fig. 5.
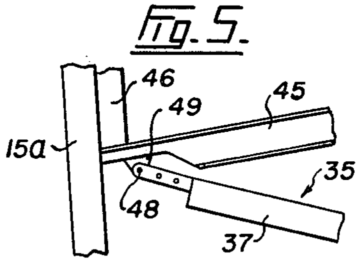
Fig. 6.
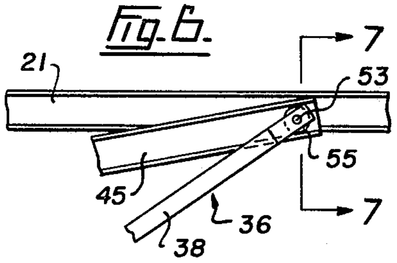
Fig. 7.
Fig. 8.
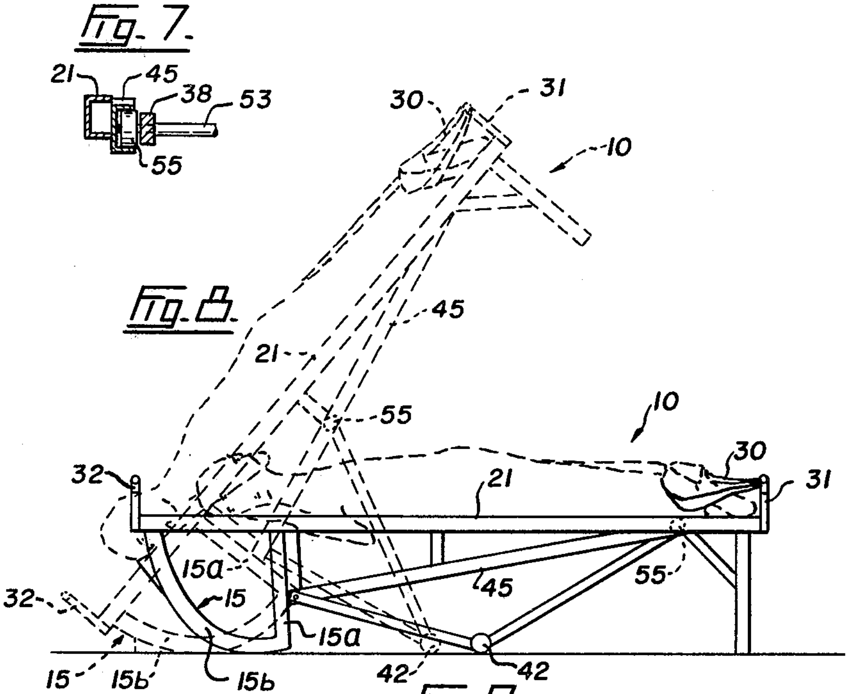
Fig. 9.
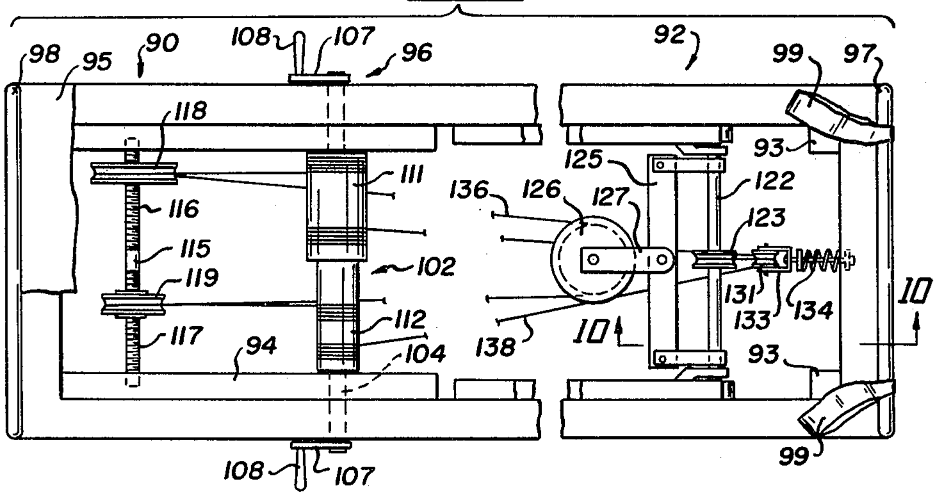

THERAPEUTIC COUCH

BACKGROUND OF THE INVENTION

The field of the invention is that of tiltable health tables and the like, this type of table being generally classified in U.S. Classes 128/71, 128/24, and 269/323.

The most pertinent prior art known to the applicant comprises U.S. Pat. No. 3,568,669 dated Mar. 9, 1971, U.S. Pat. No. 3,797,050 dated Mar. 19, 1974, U.S. Pat. No. 1,820,436 dated Aug. 25, 1931, U.S. Pat. No. 893,031 dated July 14, 1908 and U.S. Pat. No. 2,983,930 dated May 16, 1961.

SUMMARY OF THE INVENTION

The present invention relates to a device which primarily is intended for use in the home or in other locations where it is not feasible to install the elaborate therapeutic equipment normally found in hospitals or other such facilities. In many instances, a person who may be alone at home during the day is required to self-administer some form of therapy. For example it is well known that periodically stretching the spine will help to relief some spinal conditions and a person suffering from a build-up fluid in the lungs is often required to have the excess fluid drained at regular intervals. This invention differs principally from the known prior art patents in that it provides a couch which can be used as such when not needed to administer spinal traction or respiratory drainage. Most individuals do not require help to use the present couch for such purposes and this applies to those who are quite handicapped or weakened to some extent by illness. One embodiment of the invention is provided with manually-operable tilting equipment which allows someone prone upon the couch to tilt and level the structure even if that person should have only limited strength in his arms. Another embodiment of the invention provides a power-operated mechanism for achieving the same tilting and levelling action which can readily be initiated by the occupant of the couch. Other advantages of this therapeutic couch will appear as the description of the two preferred embodiments develops.

BRIEF DESCRIPTION OF THE DRAWINGS

FIG. 5 is a detail side elevation of one end of the lever assembly, FIG. 6 is a vertical section taken on the line 6—6 of FIG. 3, FIG. 7 is a vertical section taken on the line 7—7 of FIG. 6, FIG. 8 is a schematic view showing the couch occupied and tilted to a position of use, FIG. 9 is a view similar to FIG. 4 but showing another embodiment of the invention.

DESCRIPTION OF THE PREFERRED EMBODIMENTS

Figure 1:
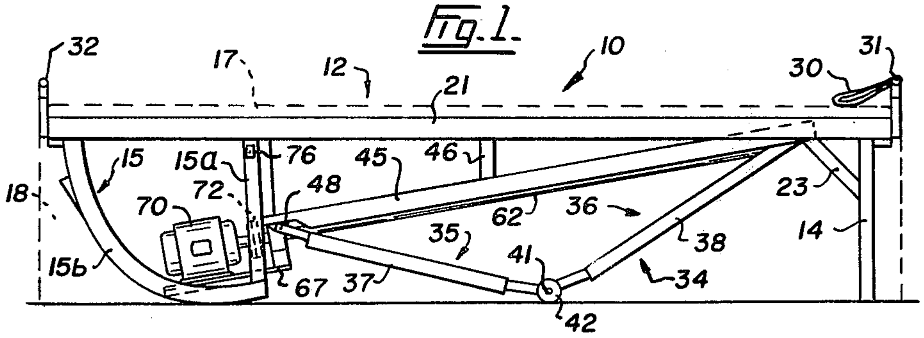
FIG. 1 is a side elevational view of the therapeutic couch constructed in accordance with the present invention.
Figure 2:
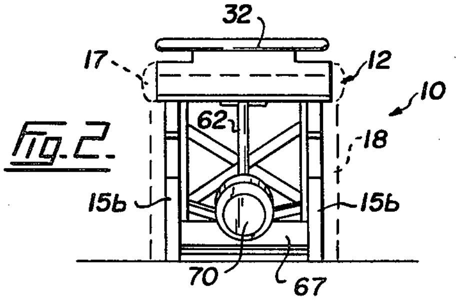
FIG. 2 is an end elevation of the couch.

Referring to the drawings, the numeral 10 indicates a preferred embodiment of the present therapeutic couch. The couch indicated generally at 10 is shown in FIGS. 1 to 8 as comprising a rectangular main frame 12 which is mounted on legs 14 and 15. A suitably padded bench 17 is carried on top of this main frame. Attached to either the frame or the bench is a skirt 18 which is shown by dotted lines only in FIGS. 1 and 2. This skirt extends down to about floor level thus enclosing all four sides of the couch and hiding the legs as well as the operating parts below the frame.

Figure 3:
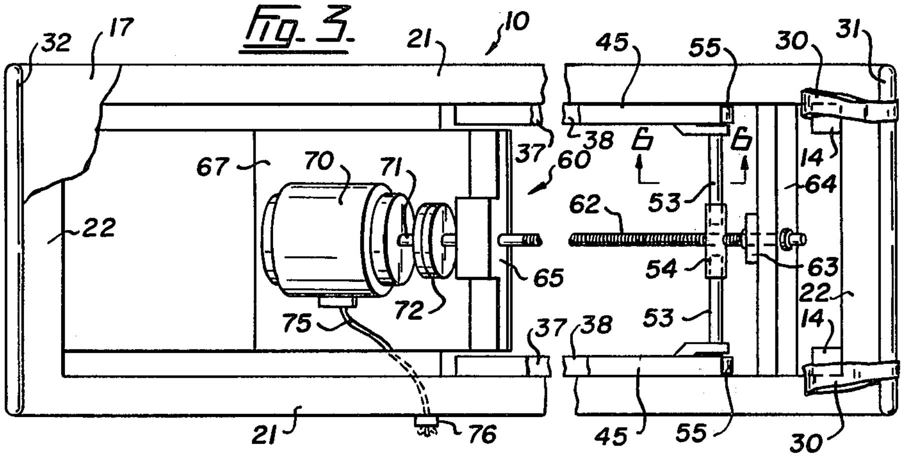
FIG. 3 is an enlarged fragmentary plan view of the couch showing portions of its rectangular frame, lever assembly and operating means for the assembly.
Figure 4:
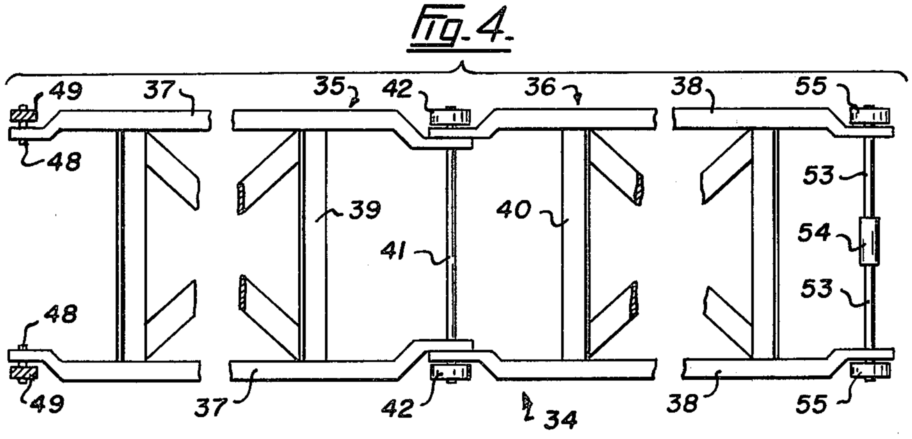
FIG. 4 is an enlarged fragmentary plan view of the lever assembly.

The pair of legs 14 at one end of the frame are secured at inside corners formed by side and end rails 21 and 22 of the main frame, see FIG. 3. Each leg 14 is also secured to one of the side rails 21 of the frame by a brace 23 which can be seen in FIG. 1.

At the other end of the frame, the pair of legs 15 are secured to the side rails 21. Each leg 15 comprises a straight and substantially vertical portion 15a located a short distance from the adjacent end rail 22 of the frame and a rocker portion 15b which curves upwardly from the lower end of the straight portion to connect with the frame. This particular leg arrangement supports the frame 12 so that normally the bench 17 is spaced a suitable distance above and parallel to the floor. When the end of the couch having the legs 14 is raised, the rocker portions 15b of the legs 15 provide an easy rolling or pivoting motion on the floor.

The therapeutic couch 10 is adapted to be unended or tilted by a person who usually lies face down on the bench 17. At this time the users ankles are adapted to be held by straps 30 which preferably are secured to a board 31 carried by the end rail 22 at the foot end of the couch. A person of normal height with this feet held against movement in this manner would have his head above the legs 15 at the opposite or head end of the couch. A similar board 32 may be provided at the head end and the padded bench 17 extends between these upwardly-projecting head and foot boards.

In order that the couch can readily be tilted when occupied in this manner, the structure is provided with a lever assembly generally indicated at 34. The assembly 34 is shown to comprise a frame-like lever 35 which is hingedly connected to a similarly-shaped lever 36. As shown best in FIG. 4, the levers 35 and 36 sometimes called lever frames, have side bars 37 and 38 which are connected together by cross bars 39 and 40. The lower overlapping ends of the side bars are hingedly connected by a transverse axle 41 which journals a pair of rollers 42 having rolling contact with the floor.

The lever assembly is attached to the main frame by a structure which includes a pair of guide rails 45 located alongside the side rails 21. These guide rails are suspended below the frame by means of suitably arranged hangers 46. The rails 45 extend between the legs 14 and 15 and it will be noticed the rails slope upwardly towards the leg 14 at the foot end of the couch. As shown best in FIGS. 4 and 5, the upper ends of the side bars 37 are connected by hinge pins 48 to bearings 49 carried by the underside of the guide rails 45 near the legs 15.

The upper ends of the side bars 38 on the frame-like lever 36 are fitted with transversely-aligned spindles 53 which are connected by a centrally-disposed nut 54. A roller 55 is mounted on each spindle and these rollers ride in the guide rails 45. Preferably, the guide rails are formed of lengths of channel iron so that the rollers 55 will roll freely between the horizontal top and bottom flanges of the channel. With the rollers 55 mounted in the guide rails in this manner, the rollers and therefore the adjoining end of the lever 36 cannot drop out of the guide rails if the foot end of the couch should be lifted off the floor.

It will be apparent the lever assembly 34 is a hinge-like structure which has an open position as shown in FIG. 1. When the assembly is folded so that the upper ends of the levers 35 and 36 are moved towards one another, the rollers 55 are caused to travel along the sloping guide rails 45 which movement results in the therapeutic couch being tilted upwardly on the legs 15 at the head end of the couch.

The assembly 34 is operated to tilt the couch 10 by means generally indicated at 60. As shown in FIG. 3, the operating means 60 comprises a threaded shaft 62 which has one end journalled in a bearing 63 carried by a cross member 64 extending between the side rails 21 of the main frame. The opposite end of this shaft rotates in a bearing 65, this bearing being carried by a shelf 67 which is supported between the legs 15. The nut 54 connecting the spindles is engaged by the threaded shaft 62. A reversible electric motor 70 is also mounted on the shelf 67 and the drive shaft 71 of this motor, which rotates at an appropriately reduced speed, is connected to the shaft 62 by means of a flexible coupling 72. The motor is included in an electric circuit 75 (FIG. 3 only) which includes a double throw switch 76 preferably mounted on one side of the frame 12. The circuit 75 is adapted to be connected to a suitable source of power (not shown) whereby a person lying prone upon the bench can operate the switch to tilt and level the couch.

The operation of the therapeutic couch 10 is believed to be apparent from the foregoing description of the device but, briefly, a person requiring spinal traction or respiratory drainage for example, lies face down on the bench 17 and places the straps 30 around his ankles. In FIG. 8, this position of use is illustrated and it will be seen the users head is close to the corresponding end of the couch and the switch 76 is within easy reach of one hand. When the switch is closed, the motor 70 is energized to rotate the shaft 62 at a suitably reduced speed and thus operate the lever assembly 34. The frame-like levers 35 and 36 are folded together as a result of rotation of the shaft and, as the rollers 55 are caused to travel along the guide rails 45, the rollers 42 move a short distance over the floor as the couch is slowly tilted on the rocker portions **15*b* of the legs to the dotted line position shown in FIG. 8. The user opens the switch 76 once he has reached the desired inclined and head-down position whereupon the tilted couch remains firmly supported by the lever assembly 34 and the legs 15 during the period required for traction or drainage. At the end of this time period, the switch 76 is operated to reverse the motor 70** and this causes the couch to return to its original position parallel to the floor.

Figure 10:
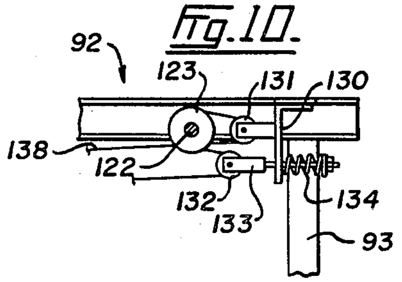
FIG. 10 is a vertical section taken on the line 10—10 of FIG. 9.
Figure 11:
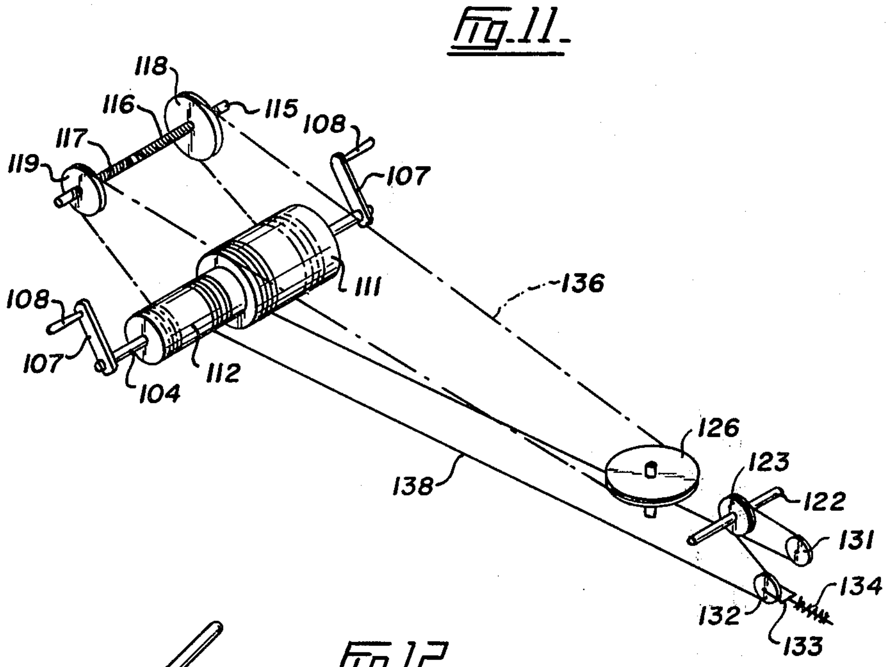
FIG. 11 is a schematic view showing details of the operating means of this embodiment.
Figure 12:
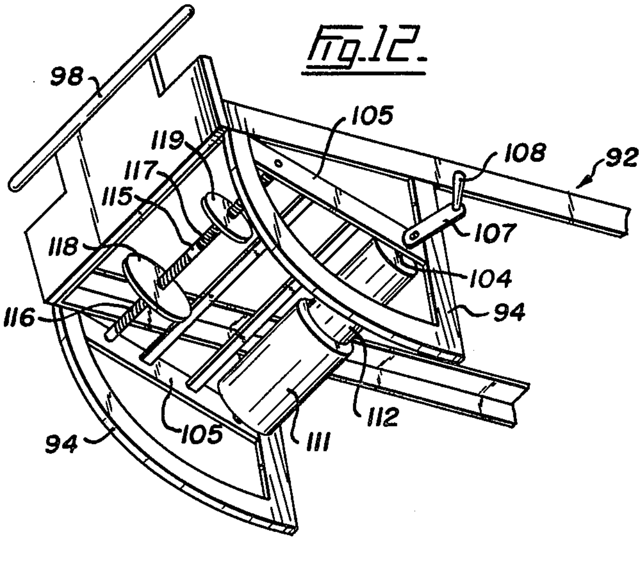
FIG. 12 is a perspective view showing one end of this embodiment.

Another preferred embodiment of the present invention comprises a manually-operated therapeutic couch which is generally indicated at 90 in FIG. 9 and details of which are shown in FIGS. 10, 11 and 12. Couch 90 has a main frame 92, legs 93 and 94, a bench 95, and a lever assembly 96 all of which are constructed substantially as previously described. Preferably, the frame 92 is fitted with foot and head boards 97 and 98 the upper edges of which project a suitable distance above the top surface of the bench. These boards may be similarly shaped and ankle straps 99 (FIG. 9) of appropriate length are secured to the foot board 97.

The couch 92 is equipped with operating means generally indicated at 102. This manually-operated means comprises a shaft 104 which is journalled in a mounting frame 105 carried by the legs 94 as shown in FIG. 12. This horizontally disposed and transversely extending shaft 104 is adapted to be rotated by means of cranks 107 which are secured to opposite ends of the shaft at the sides of the frame. The cranks 107 extend in the same direction and are each fitted with a handle 108 which is foldable into alignment with the crank when not in use. Large and small winding drums 111 and 112 are non-rotatably secured to the shaft 104. Another shaft 115, is non-rotatably mounted in the frame 105 near the head end of the couch. This transverse shaft 115 has opposite threads 116 and 117 which are threadedly engaged by large and small pulleys 118 and 119. In this embodiment, the rollers 55 on the lever assembly are mounted on an axle 122 on which a pulley 123 is rotatably mounted. The axle is fitted with a yoke 125 and a horizontally disposed pulley 126 is connected to this yoke by a pivot arm 127. The frame 92 supports a bracket (130, see particularly FIG. 10) near the legs 93 and a small pulley 131 is rotatably carried by this bracket. Below the pulley 131, another pulley 132 of the same size is rotatably mounted on a horizontal plunger 133 which slidably extends through the bracket 130. A compression spring 134 is fitted to the plunger to urge the pulley 132 towards the foot end of the frame 92.

The two winding drums and the several pulleys mentioned above are wound with a main cable 136 in a manner which will be best understood with reference to FIG. 11. One end of the main cable is secured to an end of the large winding drum 111 near the side rail of the frame. This end of the cable makes a few turns around the large winding drum and then extends around the large pulley 118 and back to pulley 126, thence around this horizontal pulley and over the small pulley 119 and then back to the small winding drum 112. The main cable is wrapped a few turns around the small winding drum in a direction opposite to the direction the opposite end of the cable is wound on the drum 111 and the cable end is secured to the drum 112 near the adjacent side of the frame 92.

Another tensioning cable 138 is trained over the pulleys 131, 123 and 132 as shown best in FIGS. 10 and 11 and one end of this cable is wrapped around and is secured to the large drum 111 at the opposite end of the drum to the cable 136 with the turns of the two cables being in the opposite direction. From the pulley 132, the cable 138 extends forward to the small drum 112 where it is wrapped a few turns around the end of the drum opposite the cable 136. The end of the tensioning cable is secured to the small drum and it will again be noted the turns of this cable are in a direction opposite to the direction of the turns of the adjacent end of the main cable. Appropriate tension is maintained on the cable 138 at this time by the pressure applied by the partially compressed spring 134.

The person using the couch 90 attaches the ankle straps 99 and assumes a face down position on the bench 95 with his arms extending down on opposite sides of the frame so that the handles 108 can be gripped in his hands. Both cranks 107 are rotated in unison in the same forward direction to wind the main cable 136 around the drums 111 and 112. This winding moves the pulley 126 forward to operate the lever assembly 96 with the result that the couch is tilted in the manner indicated in FIG. 8. Because of the mechanical advantage provided by the winding system the effort required to tilt the couch is not very great and, of course, it is a simple matter for the user to return the device and himself to a horizontal position. The tensioning cable 138 and associated parts ensure that the main cable 130 cannot become slack so as to dislodge from the pulleys or otherwise fouled around the winding drums.

From the foregoing, it will be apparent either of the therapeutic couches 10 or 90 can be operated by the person who is required to undergo spinal traction or respiratory drainage. This can be done even when that person is somewhat limited in the movements he can make because of pain or discomfort or the fact that he is physically handicapped.

I claim:

1. A therapeutic couch comprising a frame having opposite ends, legs at the opposite ends normally supporting the frame in the horizontal position above a floor, the legs at one end including rocker portions normally having rolling contact with the floor, a bench mounted on the frame to accomodate a person in the prone position, a lever assembly on the underside of the frame, and operating means on the frame for moving the lever assembly relative to the frame and the floor so as to upend the frame on the lever assembly and the rocker portions of the legs at the one end of the frame, to a selected tilted position.

2. A therapeutic couch as claimed in claim 1, in which said lever assembly comprises first and second levers having lower and upper ends, hinge means interconnecting the lower ends of the first and second levers, other hinge means connecting the upper end of the first lever to the frame, guide means attaching the upper end of the second lever to the frame for movement longitudinally of said frame, said first and second levers being moved towards and away from one another by the operating means to move the frame between the tilted and horizontal positions.

3. A therapeutic couch as claimed in claim 2, in which said operating means comprises a reversible electric motor having a drive shaft, a threaded driven shaft operatively connected at one end to the drive shaft, a nut carried by the lever assembly in engagement with the threaded driven shaft, and circuit means including a control switch for connecting the reversible electric motor to a source of power.

4. A therapeutic couch as claimed in claim 2, in which said operating means comprises a winding system including crank-operated winding drums rotatable by the person on the bench.

5. A therapeutic couch as described in claim 2 additionally comprising rollers rotatably mounted on the hinge means interconnecting the lower ends of the first and second levers, so as to normally contact the floor.

6. A therapeutic couch comprising a frame having opposite ends, legs at the opposite ends normally supporting the frame in a horizontal position above the floor, the legs at one end including rocker portions normally having rolling contact with the floor, said frame having at least one guide rail between the legs at the opposite ends, a lever assembly on the underside of the frame, said lever assembly comprising a first and a second lever frame, each lever frame having lower and upper ends, hinge means interconnecting the lower ends for pivotal movement about an axis extending transversely of said lever frames another hinge means connecting the upper end of the first and second lever frames to said at least one guide rail for pivotal movement about another axis extending transversely of said lever frames, a roller carried by the upper end of said lever frames in rolling engagement with said at least guide rail, and operating means on the frame for moving the upper end of said first and second lever frames together so as to upend the frame on the lever assembly and the rocker portions of the legs at the one end of said frame, to a selected tilted position and away from each other to move said frame to said horizontal position.

7. A therapeutic couch as described in claim 6 additionally comprising rollers rotatably mounted on the hinge means interconnecting the lower ends of the first and second lever frames, so as to normally contact the floor.

* * * * *